(12) United States Patent
Nishizawa

(10) Patent No.: US 11,504,498 B2
(45) Date of Patent: Nov. 22, 2022

(54) GRIP DETECTION SENSOR

(71) Applicant: Murata Manufacturing Co., Ltd., Nagaokakyo (JP)

(72) Inventor: Yoshihiko Nishizawa, Nagaokakyo (JP)

(73) Assignee: MURATA MANUFACTURING CO., LTD., Nagaokakyo (JP)

(*) Notice: Subject to any disclaimer, the term of this patent is extended or adjusted under 35 U.S.C. 154(b) by 891 days.

(21) Appl. No.: 16/384,189

(22) Filed: Apr. 15, 2019

(65) Prior Publication Data

US 2019/0240449 A1 Aug. 8, 2019

Related U.S. Application Data

(63) Continuation of application No. PCT/JP2018/000625, filed on Jan. 12, 2018.

(30) Foreign Application Priority Data

Mar. 24, 2017 (JP) .............................. JP2017-058919

(51) Int. Cl.
G06F 3/0354 (2013.01)
A61M 25/00 (2006.01)
H01L 41/047 (2006.01)
H01L 41/113 (2006.01)
A61J 15/00 (2006.01)
H01L 41/193 (2006.01)

(52) U.S. Cl.
CPC ...... A61M 25/0043 (2013.01); A61J 15/0084 (2015.05); H01L 41/0478 (2013.01); H01L 41/1132 (2013.01); H01L 41/193 (2013.01); A61M 2025/006 (2013.01); A61M 2205/0294 (2013.01); A61M 2205/18 (2013.01)

(58) Field of Classification Search
None
See application file for complete search history.

(56) References Cited

U.S. PATENT DOCUMENTS

| 2005/0134470 | A1 | 6/2005 | Bos |
| 2006/0232378 | A1 | 10/2006 | Ogino et al. |
| 2018/0356912 | A1* | 12/2018 | Yamaguchi ............... G01L 1/16 |
| 2019/0273199 | A1* | 9/2019 | Tajitsu ................... D03D 15/41 |

FOREIGN PATENT DOCUMENTS

| JP | 2001340454 A | 12/2001 |
| JP | 2005098016 A | 4/2005 |
| JP | 2005532559 A | 10/2005 |
| JP | 2006153842 A | 6/2006 |
| JP | 2009020032 A | 1/2009 |
| WO | 2010037559 A1 | 4/2010 |

OTHER PUBLICATIONS

International Search Report issued for PCT/JP2018/000625, dated Apr. 3, 2018.

* cited by examiner

Primary Examiner — An T Nguyen
(74) Attorney, Agent, or Firm — ArentFox Schiff LLP

(57) ABSTRACT

A grip detection sensor that includes: a piezoelectric film having a first main surface and a second main surface, either one of the first main surface and the second main surface being disposed at least partly on a periphery of a linearly shaped flexible object, a first electrode on the first main surface, a second electrode on the second main surface, and a spacer configured to maintain a space between the object and the piezoelectric film.

19 Claims, 10 Drawing Sheets

GRIP DETECTION SENSOR

CROSS-REFERENCE TO RELATED APPLICATIONS

The present application is a continuation of PCT/JP2018/000625 filed Jan. 12, 2018 which claims priority to Japanese Patent Application No. 2017-058919, filed Mar. 24, 2017, the entire contents of each of which are incorporated herein by reference.

TECHNICAL FIELD

One embodiment according to the present disclosure relates to a grip detection sensor configured to detect that an object is gripped.

BACKGROUND ART

Japanese Patent Application No. 2001-340454 (Patent Document 1) discloses an apparatus for preventing pulling out a tube capable of delaying or preventing pulling out a tube by a patient or the like, the tube being attached to a human body at the time of nutritional supplementation, blood transfusion, intravenous drip, or the like, or capable of warning a patient, a caregiver or the like of a pulling out movement of the tube. The apparatus for preventing pulling out of a tube disclosed in Patent Document 1 is configured by covering a part of a tube to be attached to a human body with an elastic cover member such that the cover member can move relative to the tube. The apparatus for preventing pulling out of a tube disclosed in Patent Document 1 includes a pressure detection means that is provided on at least a part of the cover member and is configured to detect application of a pressure of a predetermined value or more and output a detection signal upon the detection. The apparatus of Patent Document 1 also includes a warning means configured to issue a warning based on the detection signal from the pressure detection means. With this configuration, a warning is issued when a pressure equal to or higher than a predetermined value is applied to the tube.

The tube described in Patent Document 1 is formed of a flexible material, which causes the sensor to react even when pressure is applied to the tube due to a simple touch, when the patient is turned over, or the like. This results in a frequent erroneous warning, because the sensor reacts even when the tube is not gripped by a patient. Thus the configuration described in Patent Document 1 cannot distinguish whether or not the tube has been gripped by a patient or moved due to some other reason.

In view of the above, there is a need for a grip detection sensor configured to appropriately detect a case where a flexible object, such as a tube, is gripped by a person.

SUMMARY

A grip detection sensor according to one embodiment of the present disclosure comprises: a piezoelectric film having a first main surface and a second main surface, either one of the first main surface and the second main surface being disposed at least partly on a periphery of a linearly shaped flexible object; a first electrode on the first main surface; a second electrode on the second main surface; and a spacer to maintain a space between the object and the piezoelectric film.

As described above, the grip detection sensor includes the piezoelectric film on at least a part of the periphery of a linearly-shaped flexible object, which enables detection of a deformation added to the piezoelectric film when the object is gripped. In addition, since the spacer maintains a space between the piezoelectric film and the object, influence of deformation is hardly transmitted to the piezoelectric film even if the object itself deforms, thereby preventing misidentification of whether or not the object is gripped.

According to one embodiment of the present disclosure, it is possible to appropriately detect a case where a person grips a flexible object, such as a tube.

DETAILED DESCRIPTION

Figure 1:
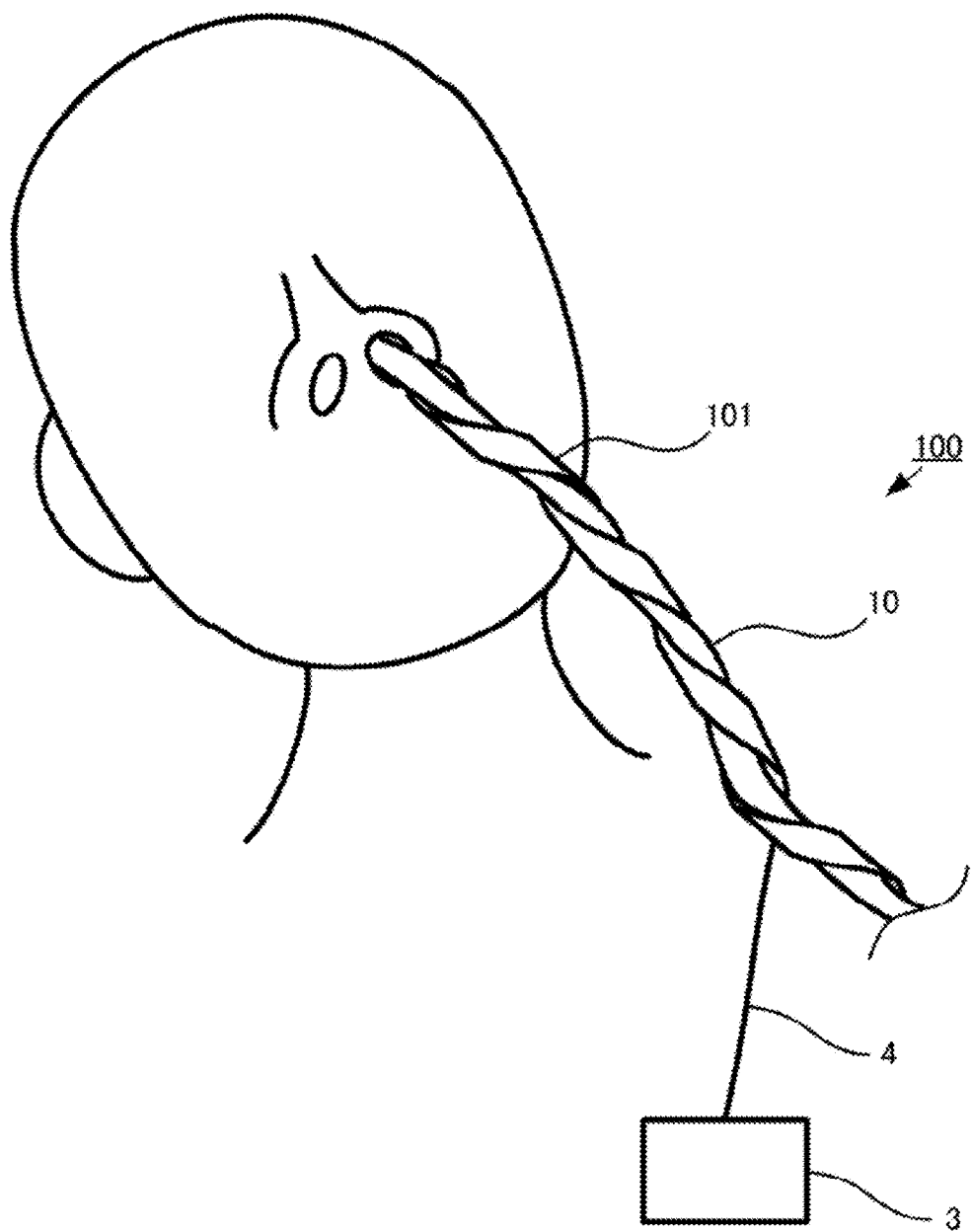
FIG. 1 is a view illustrating a condition of use of a grip detection sensor according to a first embodiment.

Hereinafter, a grip detection sensor according to an embodiment of the present disclosure is described with reference to the drawings. It should be noted that the grip detection sensor shown in each figure in the drawings is merely an example, and the disclosure is not limited thereto and can be appropriately changed in accordance with this disclosure.

FIG. 1 is a view illustrating a condition of use of a grip detection sensor 100 according to a first embodiment. As shown in FIG. 1, the grip detection sensor 100 is used while attached to a linearly-shaped flexible object. According to some examples, the flexible object may be a tracheostomy tube, a central venous catheter, a feeding tube, or the like. The first embodiment describes an example in which the grip detection sensor 100 is applied to a feeding tube 10 (hereinafter referred to as a tube 10).

FIG. 1 illustrates the tube 10 as applied to a patient. The grip detection sensor 100 is attached to the tube 10 and also connected to a processing unit 3. The grip detection sensor 100 and the processing unit 3 are electrically connected with each other through a wiring 4, according to this aspect. Note that the grip detection sensor 100 and the processing unit 3 may communicate with each other by radio or the like without using the wiring 4.

Further, in this embodiment the grip detection sensor 100 may be connected to a power supply unit (not shown), and supply of electric power to the grip detection sensor 100 is controlled by turning the power supply unit on or off. A known power supply source, such as a dry battery, a domestic power supply, a solar battery or the like may be employed.

In this first embodiment, the grip detection sensor 100 is used while wound around the tube 10. The grip detection sensor 100 is provided at least as part of a periphery of the tube 10 and in an area that is easily accessible by a patient. This configuration makes it possible to detect more accurately whether or not the tube 10 is gripped by a hand of a patient. It should be noted that the grip detection sensor 100 may be provided not only at a part of the periphery of the tube 10 but also entirely around the tube 10 in an axial direction of the tube 10.

Figure 2:
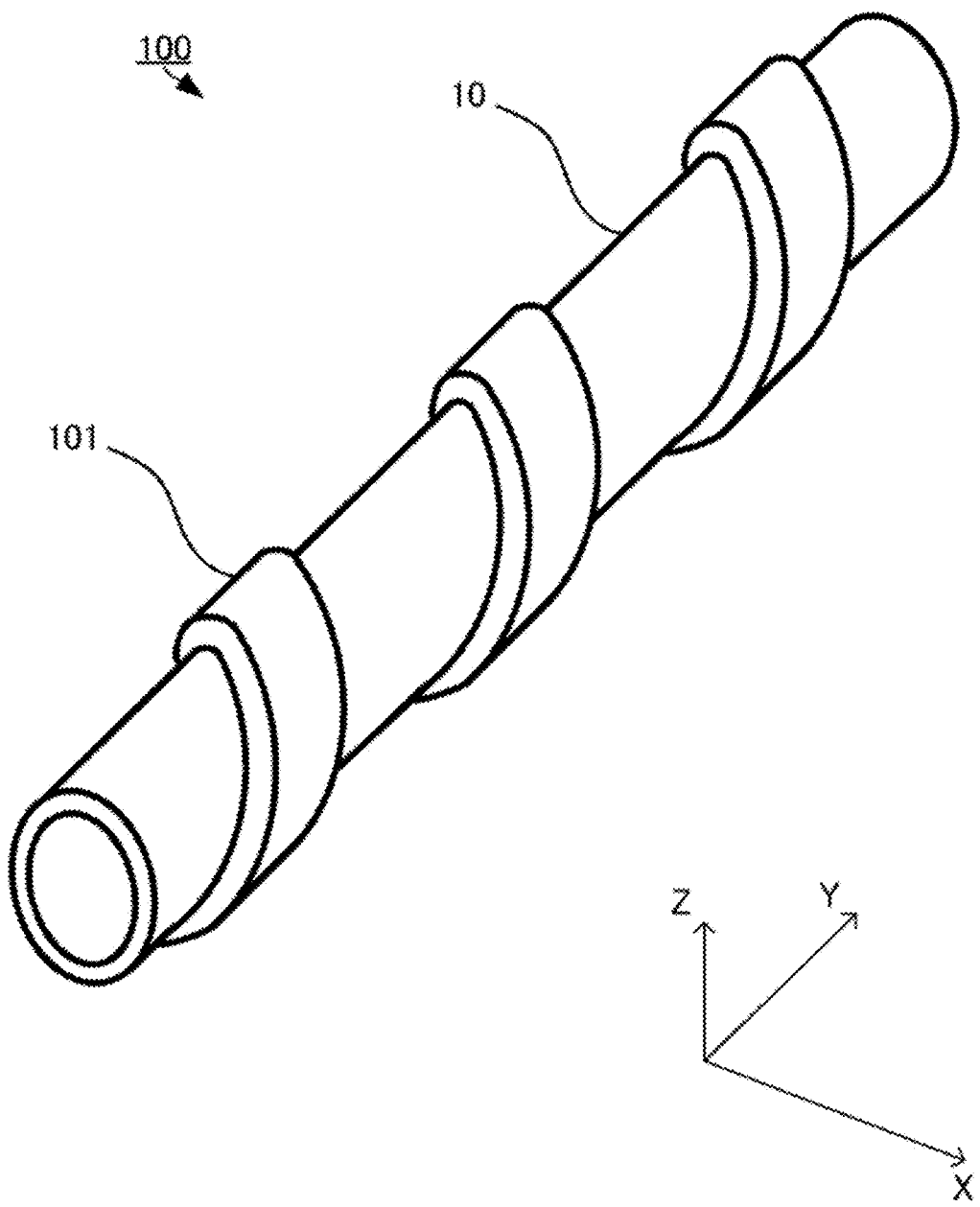
FIG. 2 is a partial perspective view of the grip detection sensor according to the first embodiment.

FIG. 2 is a partial perspective view of the grip detection sensor 100 according to the first embodiment.

Figure 3A:
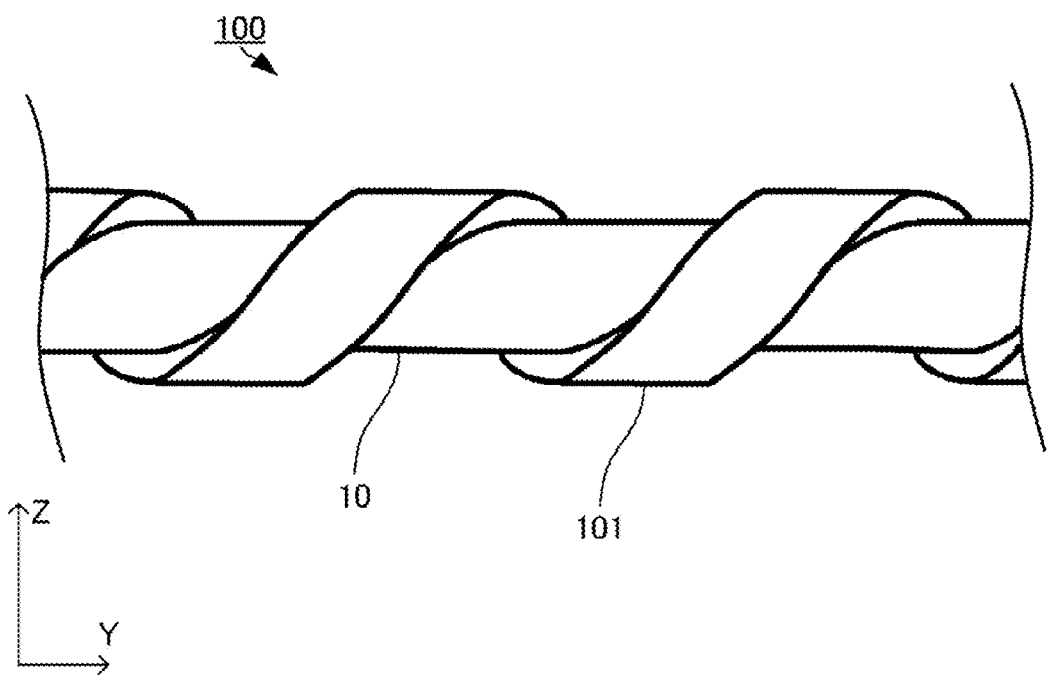
FIG. 3(A) is a partial side view of the grip detection sensor according to the first embodiment.
Figure 3B:
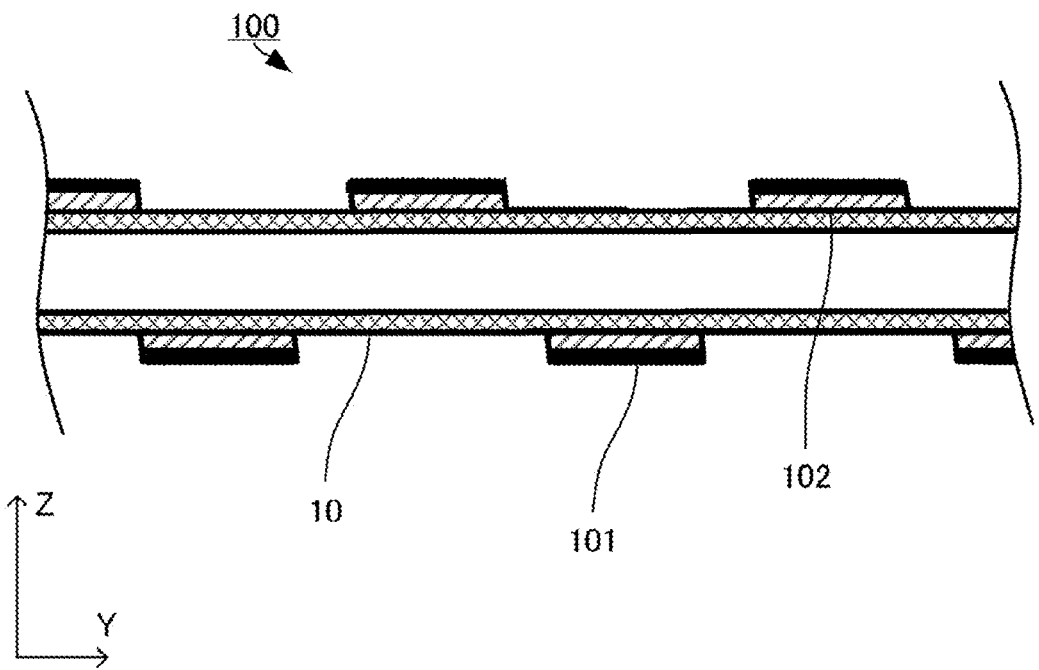
FIG. 3(B) is a schematic sectional view of the grip detection sensor according to the first embodiment taken along a line parallel to an axis of the grip detection sensor.
Figure 4A:
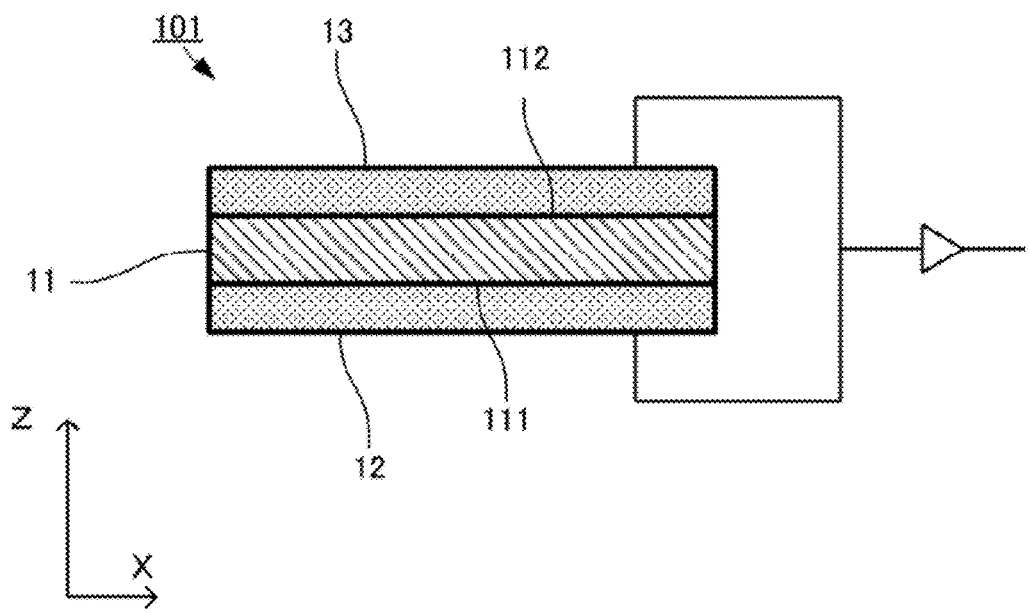
FIG. 4(A) is a schematic view illustrating a piezoelectric element according to the first embodiment.
Figure 4B:
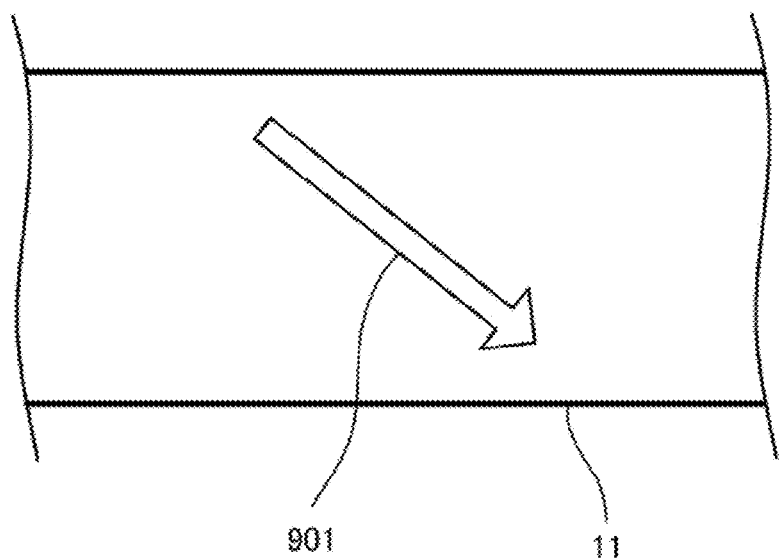
FIG. 4(B) is a schematic view illustrating a piezoelectric film according to the first embodiment.

FIG. 3(A) illustrates a partial side view of the grip detection sensor 100 according to the first embodiment. FIG. 3(B) is a schematic sectional view of the grip detection sensor 100 according to the first embodiment taken along a line parallel to an axis of the grip detection sensor. FIG. 4(A) is a schematic view of the grip detection sensor 100 illustrating a piezoelectric element 101 according to the first embodiment. FIG. 4(B) is a schematic view illustrating a piezoelectric film 11 according to the first embodiment. In FIGS. 2, 3(A), and 3(B), wiring and the like drawn out from electrodes and the like are omitted.

In FIGS. 2 to 10(B), the axial direction of the tube 10 is defined as a Y-axis direction, a vertical direction is defined as a Z-axis direction, and a direction perpendicular to both the Y-axis and the Z-axis is defined as an X-axis direction. For convenience of explanation, the piezoelectric element 101 and the piezoelectric film 11 have flat surfaces in FIGS. 4(A) and 4(B), but they may be curved along an outer surface of the tube 10 according to embodiments of the present disclosure.

As shown in FIGS. 2, 3(A) and 3(B), the grip detection sensor 100 comprises the piezoelectric element 101 and a spacer 102. As shown in FIG. 4(A), the piezoelectric element 101 includes the piezoelectric film 11, a first electrode 12, and a second electrode 13. The piezoelectric film 11 has a first main surface 111 and a second main surface 112. The piezoelectric element 101 is overlaid with and adhered to a surface of the spacer 102 provided around the tube 10. The piezoelectric film 11 is spirally wound around the tube 10 such that the first main surface 111 faces the tube 10. Since the piezoelectric film 11 is wound around the tube 10, the piezoelectric film 11 can be formed of a single rectangular sheet and thus can be easily manufactured. The piezoelectric film 11 is not limited to a rectangular shape however, and may be configured into any shape that is designed appropriately according to the shape of the tube 10, such as a wave shape or the like.

The spacer 102 is provided between the tube 10 and the piezoelectric element 101 to maintain a space of a predetermined range of dimensions between the tube 10 and the piezoelectric film 11. The tube 10, the spacer 102, and the piezoelectric film 11 are bonded by using an adhesive or a tape, for example.

The spacer 102 preferably has lower rigidity than the tube 10 (an object). Since the spacer 102 has lower rigidity than the tube 10, the spacer 102 can effectively absorb a bend of the tube 10 when the tube 10 itself is bent due to vibration or the like. As a result, deformation of the piezoelectric film 11 can be further suppressed, preventing the grip detection sensor 100 from frequently generating erroneous output signals. Thus, the grip detection sensor 100 can more accurately detect that the tube 10 is gripped by a patient, as compared to previously described configurations.

The spacer 102 may comprise a cushioning material having flexibility according to some embodiments.

The spacer 102 may, according to some embodiments, have a sponge-like structure. Examples of the material of the spacer 102 are urethane-based resins, melamine-based resins, rubbers, and the like, though other materials are also contemplated by the present disclosure.

The rigidity of the spacer 102 can be changed by changing the material, the shape, or the like of the spacer 102. Thus, even in the case where the spacer 102 and the tube 10 are formed of the same material, the rigidity of the tube 10 and the spacer 102 can be made different from each other by forming the material of the spacer 102. In the case where the tube 10 and the spacer 102 are formed of the same material, the tube 10 and the spacer 102 may be fused together in this embodiment eliminating the need for an adhesive, a tape, or the like for bonding.

The first electrode 12 is provided on the first main surface 111 of the piezoelectric film 11, and the second electrode 13 is provided on the second main surface 112 of the piezoelectric film 11. The first electrode 12 may be a GND electrode and the second electrode 13 may be a signal electrode. The first electrode 12 and the second electrode 13 may be, for example, an inorganic electrode, such as ITO, ZnO, silver nanowire, carbon nanotube, graphene, or the like, or an organic electrode mainly composed of polythiophene, polyaniline or the like, though other materials are also contemplated by the present disclosure. By using such a material, the signal electrode and the GND electrode may be transparent electrodes. Use of a transparent material as the piezoelectric film 11 and the spacer 102 increases the transparency of the grip detection sensor 100. Due to the transparency, the condition of the tube 10 may be easily checked even when the grip detection sensor 100 is attached to the tube 10. In addition, the tube 10 looks the same as ordinary tubes when the grip detection sensor 100 is transparent, which prevents a patient from feeling uncomfortable. It should be noted that the piezoelectric film 11 is not necessarily transparent, and may be formed of a material, such as silver, copper, and aluminum.

The piezoelectric film 11 may be any film having piezoelectricity, and is formed of, for example, uniaxially stretched polylactic acid (PLA), and more preferably poly-L-lactic acid (PLLA).

In the present embodiment, the piezoelectric film 11 is formed of uniaxially stretched poly-L-lactic acid (PLLA). The piezoelectric film 11 is uniaxially stretched in a direction substantially parallel to the diagonal line of the rectangular shape (see the arrow shown in FIG. 4(B)).

Hereinafter, this direction is referred to as a uniaxial stretching direction 901. The uniaxial stretching direction 901 preferably forms an angle of 45° with respect to the axial direction or the transverse direction of the piezoelectric film 11. However, the angle is not limited thereto, and may be designed to be an optimum angle in view of the characteristics and a condition of use of the piezoelectric film 11. For example, the uniaxial stretching direction may form an angle of 45° with respect to a bending direction of the piezoelectric film 11.

It should be noted that an angle of the uniaxial stretching direction is not limited to exact 45° and may be about 45°.

About 45° includes an angle of 45°±about 10°, for example. These angles are appropriately determined according to the overall design, such as detection accuracy, based on a purpose of the grip detection sensor 100. Further, an angle of the uniaxial stretching direction is not limited to about 45°, and the present disclosure may employ any angle that can detect deformation.

The aforementioned PLLA is a chiral polymer, and has a main chain with a helical structure. Such PLLA exhibits piezoelectricity when the molecules are oriented by uniaxially stretching. Then, the uniaxially stretched PLLA generates charges due to deformation of the flat film surface of the piezoelectric film 11. In this case, the amount of charges to be generated is uniquely determined by the amount of displacement that the flat film surface is displaced in a direction orthogonal to the flat film surface by pressing. A piezoelectric constant of the uniaxially stretched PLLA belongs to a group of very high piezoelectric constants among polymers.

Thus, using PLLA makes it possible to detect deformation transmitted to the piezoelectric film 11 with high sensitivity and reliability. That is, the deformation applied to the piezoelectric film 11 can be reliably detected as compared to known configurations.

A stretch ratio is preferably about 3 to 8. Heat treatment is performed after stretching to grow extended chain crystals of polylactic acid, which enhances the piezoelectric constant. In the case of biaxial stretching, the same effects as the uniaxial stretching can be obtained by stretching the two axes at different stretch ratios. For example, when a given direction is defined as an X-axis and the piezoelectric film 11 is biaxially stretched at a stretch ratio of 8 in the X-axis direction and at a stretch ratio of 2 in a Y-axis direction that is orthogonal to the X-axis direction, the same effects on the piezoelectric constant can be obtained as in the case where the piezoelectric film 11 is uniaxially stretched at a stretch ratio of 4 in the X-axis direction. The films simply subjected to uniaxially stretching are liable to tear along the stretching axis direction, but the strength thereof can be enhanced to a certain degree by being subjected to the biaxial stretching as described above.

Further, the PLLA exhibits piezoelectricity as a result of a molecular orientation treatment, such as stretching, and does not require a poling treatment unlike other polymers such as PVDF or piezoelectric ceramics. Unlike ferroelectrics such as PVDF or PZT, the piezoelectricity of PLLA which does not belong to ferroelectrics is exhibited not by ion polarization, but derives from a helical structure which is a characteristic structure of the molecules of PLLA.

Hence, PLLA does not exhibit pyroelectricity that other piezoelectric bodies having ferroelectricity exhibit. Thus, PLLA is suitable for use on an object touched by a living body. Further, a piezoelectric constant of PLLA is very stable over time, while a piezoelectric constant of PVDF or the like fluctuates with time and significantly lowers in some cases. Consequently, it is possible to detect deformation of the piezoelectric film 11 with a high sensitivity without influence of surrounding environment. In the case where a piezoelectric film having pyroelectricity, such as PVDF, is used instead of PLLA, a grip without strength may not be detected, or even a slight touch may be detected depending on an ambient temperature. PVDF can be used in the case where a sensor is not susceptible to a surrounding environment (a sensor with low sensitivity). Further, PVDF can also be used in the case where a sensor for detecting the ambient temperature is additionally prepared and the sensitivity of the piezoelectric element is adjusted according to the ambient temperature. However, a system using PLLA can be more simplified than a system using PVDF.

In some embodiments, the piezoelectric element may have a laminated structure including the first electrode 12, the piezoelectric film 11, the second electrode 13, an insulating film (not shown), and a third electrode (not shown). In this case, the first electrode 12 and the third electrode are GND electrodes and the second electrode 13 is a signal electrode. In this piezoelectric element, the GND electrodes (the first electrode 12 and the third electrode) are disposed so as to cover the second electrode 13 which is the signal electrode. Such a configuration where the first and third electrode are disposed to cover the second electrode 13 reduces malfunctions caused by noise generated from the hand, noise emitted from peripheral devices, etc. The insulating film may be a PET film or a polyimide film. A piezoelectric film may be used to increase the sensitivity to gripping. In this case, the sensitivity to gripping can be increased by placing both of the piezoelectric films in a direction in which the uniaxial stretching direction of PLLA forms an angle of 45°. Further, various deformations can be detected by placing one of the piezoelectric films in a direction in which the uniaxial stretching direction of PLLA forms an angle of 0° and the other one of the piezoelectric films in a direction in which the uniaxial stretching direction of PLLA forms an angle of 45°.

Figure 5A:
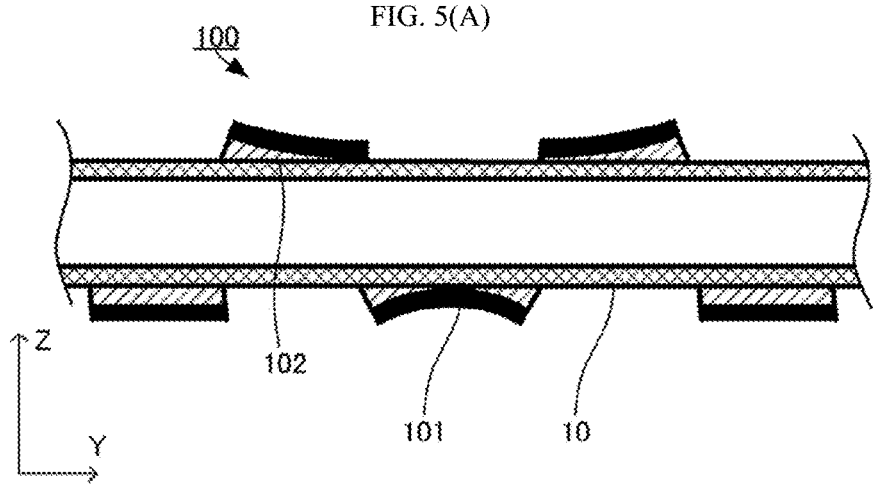
FIGS. 5(A) and 5(B) are schematic sectional views illustrating a state in which the grip detection sensor according to the first embodiment is gripped.
Figure 5B:
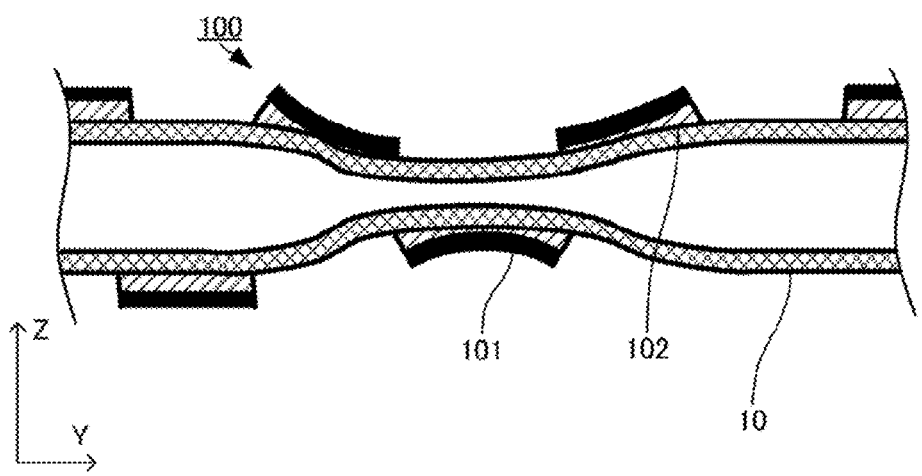
Figure 5C:
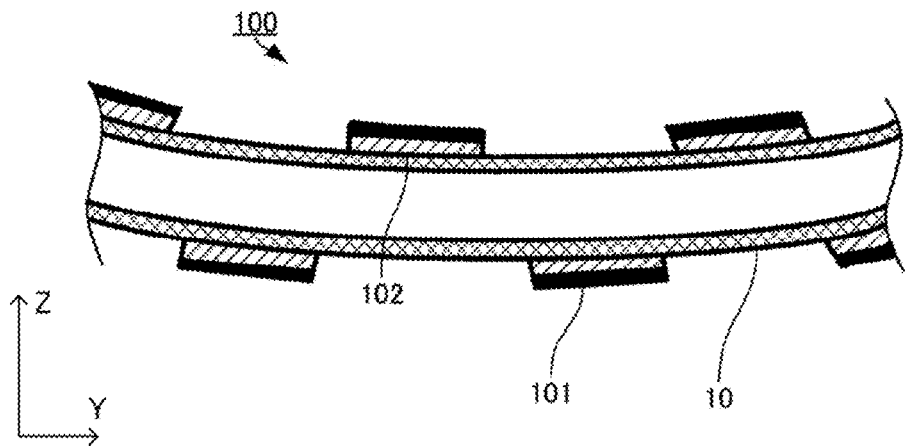
FIG. 5(C) is a schematic sectional view illustrating a state of the grip detection sensor when an object according to the first embodiment is curved.

FIGS. 5(A) and 5(B) are schematic sectional views illustrating a state in which the grip detection sensor 100 according to the first embodiment is gripped. FIG. 5(C) is a schematic sectional view illustrating a state of the grip detection sensor 100 when the tube 10 (an object) according to the first embodiment is curved. In FIGS. 5(A) to 5(C), only the tube 10, the spacer 102, and the piezoelectric film 11 are shown for convenience of explanation.

When a patient grips the tube 10, the spacer 102 wound around the tube 10 initially receives a force and deforms as shown in FIG. 5(A). As the piezoelectric film 11 also receives the force simultaneously with the deformation of the spacer 102, the piezoelectric film 11 deforms. This causes the grip detection sensor 100 to output an output signal. When the force with which the patient grips the tube 10 becomes stronger, the tube 10 deforms together with the spacer 102 and the piezoelectric film 11, as shown in FIG. 5(B). This causes the grip detection sensor 100 to output an output signal. Thus, the piezoelectric film 11 can detect the additional deformation. The processing unit 3 detects the deformation detected by the piezoelectric film 11.

As shown in FIG. 5(C), the spacer 102 wound around the tube 10 absorbs a bend of the tube 10 when the tube 10 itself is bent due to vibration or the like. Since the spacer 102 reduces vibration or the like of the tube 10, the piezoelectric film 11 deforms significantly less than previously known configurations. When the tube 10 itself is bent, the grip detection sensor 100 does not output an output signal. Thus, the grip detection sensor 100 can accurately detect the case where the tube 10 is gripped by a patient while ignoring deformation of the tube 10 when the tube is merely bent.

On the other hand, if the spacer 102 is not provided, when the tube 10 itself is bent due to vibration or the like the piezoelectric film 11 will also deform by receiving a force according to the bend of the tube 10 itself. Such a grip detection sensor would output an output signal. In the embodiments described in the present disclosure, when a patient grips the tube 10, the spacer 102 wound around the tube 10 also receives a force and deforms. As the piezoelectric film 11 also receives the force simultaneously with the deformation of the spacer 102, the piezoelectric film 11 deforms. If the spacer 102 is not provided, however, it cannot be properly detected whether or not a patient grips the tube because the output signal is output from the grip detection sensor 100 even in the case when a patient does not grip the tube 10.

An example of the processing unit 3 is an integrated circuit (IC) chip. The processing unit 3 records a voltage value output from the grip detection sensor 100 as a signal on a time axis.

The processing unit 3 determines whether or not the tube 10 is gripped based on a peak voltage value output from the grip detection sensor 100. In this case, whether or not a patient grips the tube 10 is determined based on whether or not the detected voltage value exceeds a threshold value stored in advance in the processing unit 3. Instead of the peak voltage value, an integral value at a predetermined time period can be used. In this case, whether or not a patient grips the tube 10 is determined based on whether or not the integral value exceeds a given threshold value. Although the processing unit 3 may be an IC chip, the processing unit 3 is not limited thereto, and may be comprised of any elements that are capable of executing the processes described in this disclosure.

The grip detection sensor 100 may include an amplifier configured to amplify the voltage output to be detected, and a band-pass filter configured to detect a certain frequency band, as needed. This makes it possible to detect the case where a patient grips the tube 10 more accurately.

In addition, the processing unit 3 comprehensively controls the grip detection sensor 100. The processing unit 3 reads operation programs stored in a program storage unit (not shown) and performs various processing operations. For example, the grip detection sensor 100 transmits detection of a change in the voltage value to the processing unit 3. When the processing unit 3 determines that the change in the voltage value is caused by the state in which a patient grips the tube 10 (e.g., the voltage exceeds an adjustable predetermined threshold voltage), the processing unit 3 issues a notification using a nurse call system. In this case, the notification by the processing unit 3 is not limited to a call system, e.g., a nurse call system, and may be issued by using known techniques for notifying a behavior of a patient.

It should be noted that the grip detection sensor 100 may detect not only deformation but also a physiological tremor as required. In a living body, minute mechanical vibration of muscles (i.e., physiological phenomena referred to as tremors) often occur. The physiological tremor is a tremor with a constant frequency within a predetermined frequency band (e.g., a band of about 5 Hz to 20 Hz). When a patient simply touches the tube 10, the physiological tremor is transmitted to the piezoelectric film 11.

The processing unit 3 determines that the grip detection sensor 100 detects a contact state where a patient is in contact with the tube 10, when the voltage output from the grip detection sensor 100 vibrates slightly at a frequency in a range of about 5 Hz to 20 Hz.

Note that the physiological tremor is a phenomenon unique to a living body. Even when a voltage is output from the grip detection sensor 100 as a result of an object other than a living body touching the tube 10, the processing unit determines that the grip detection sensor 100 has not detected the contact state when a frequency component cannot be detected within a predetermined frequency band.

This enables detection of the contact state where a patient is in contact with the tube 10 when the voltage value is output from the grip detection sensor 100 and the frequency component derived from the physiological tremor is detected. The processor unit 3 can then issue a notification to a call system. Thus, even when the force of an additional object is applied to the tube 10, the processing unit 3 can distinguish the case where the patient is in contact with the tube 10 from the case where some other things or the like are on the tube 10, which suppresses unnecessary nurse calls or the like. Further, unnecessary power consumption can be reduced by setting integration of the voltage values to be performed only when the physiological tremor is detected.

Figure 6:
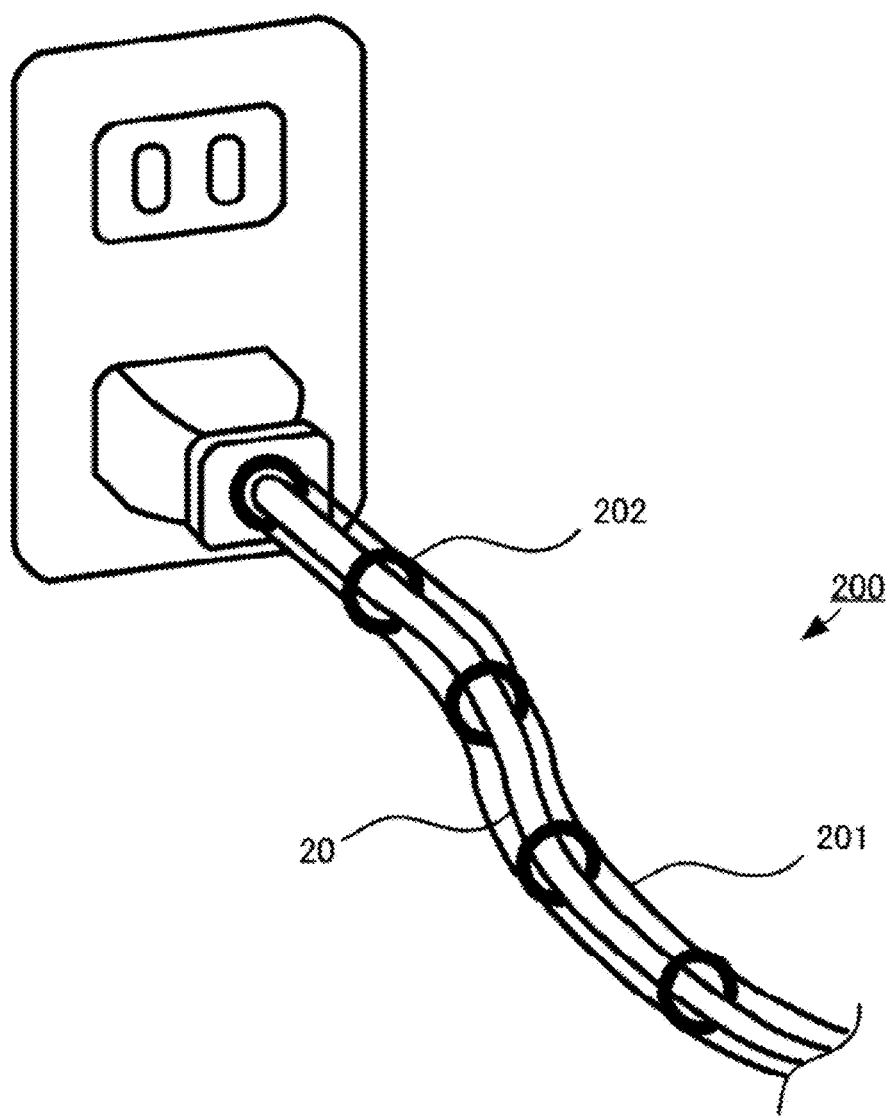
FIG. 6 is a view illustrating a condition of use of a grip detection sensor according to a second embodiment.
Figure 7A:
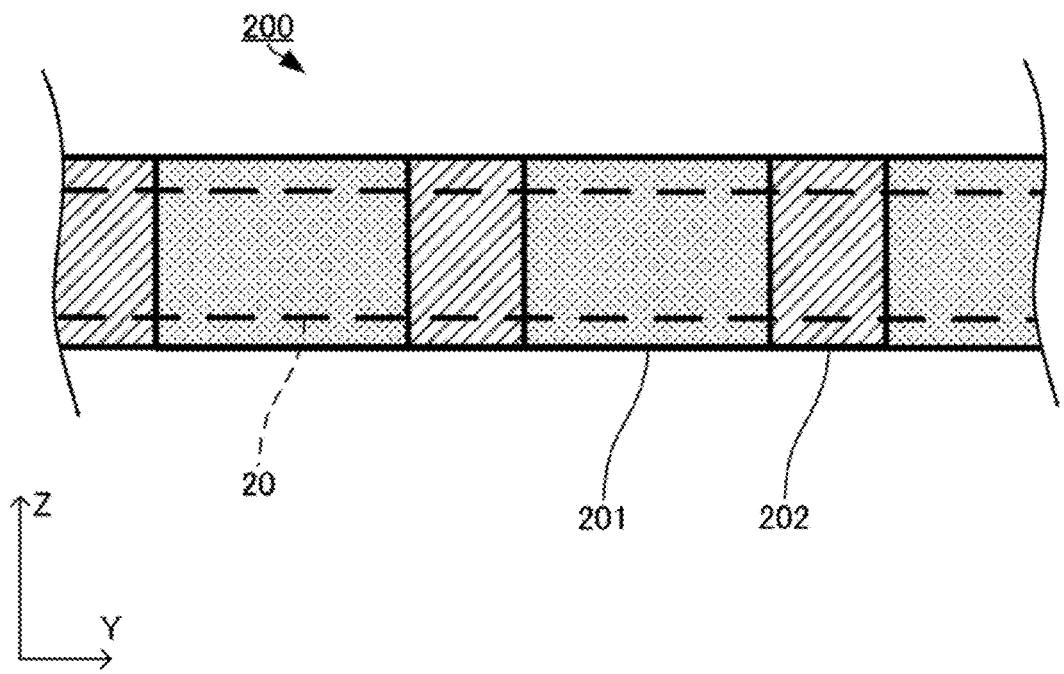
FIG. 7(A) is a partial side view of the grip detection sensor according to the second embodiment.
Figure 7B:
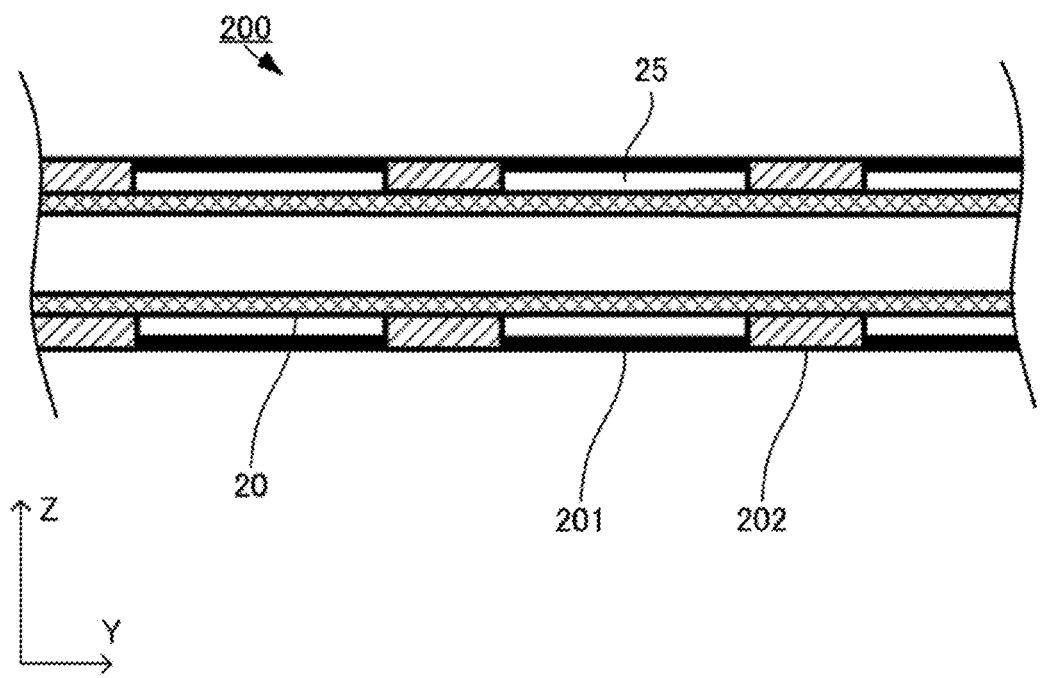
FIG. 7(B) is a schematic sectional view of the grip detection sensor according to the second embodiment taken along a line parallel to an axis of the grip detection sensor.

FIG. 6 is a view illustrating a condition of use of a grip detection sensor 200 according to a second embodiment. FIG. 7(A) is a partial side view of the grip detection sensor 200 according to the second embodiment. FIG. 7(B) is a schematic sectional view of the grip detection sensor 200 according to the second embodiment taken along a line parallel to an axis of the grip detection sensor. In the description of the second embodiment, the description of the same structure as that of the first embodiment is omitted.

As shown in FIG. 6, the grip detection sensor 200 is used while being attached to the periphery of a power cord 20 that is an object of interest. The grip detection sensor 200 is preferably provided at not only a part of the periphery of the power cord 20 but entirely around the power cord 20 in an axial direction of the power cord 20. With this configuration, even when any portion of the power cord 20 is gripped, the grip detection sensor 200 can detect the gripping.

As shown in FIGS. 6, 7(A), and 7(B), the grip detection sensor 200 includes a piezoelectric element 201 and spacers 202. Each of the spacers 202 has an annular shape and is formed on the surface of the power cord 20 so as to wind around the power cord 20. The plurality of spacers 202 are provided at intervals in the axial direction of the power cord 20. The piezoelectric element 201 is provided to surround the periphery of the power cord 20 so as to connect the spacers 202 with each other. Thus, a gap 25 is provided between the piezoelectric element 201 and the power cord 20. It is preferable that the spacers 202 are arranged at intervals that allow the piezoelectric element 201 to sufficiently deform when a force is externally applied to the piezoelectric element 201. With this configuration, the piezoelectric element 201 deforms easily when receiving an external force.

When the power cord 20 is gripped by a child or the like, a force is applied to the piezoelectric element 201 wound around the power cord 20, and the piezoelectric film of the piezoelectric element 201 deforms. This causes the grip detection sensor 200 to output an output signal. With this configuration, the grip detection sensor 200 can detect an added deformation.

In addition, when the power cord 20 itself is bent due to vibration or the like, the spacers 202 wound around the power cord 20 absorbs the bend of the power cord 20.

Since the spacer 202 reduces vibration or the like of the power cord 20, the piezoelectric film of the piezoelectric element 201 hardly deforms, or deforms less than a predetermined threshold value of deformation. When the power cord 20 itself is bent, no output signal is output from the grip detection sensor 200. With this configuration, the grip detection sensor 200 can appropriately detect a case where the power cord 20 is gripped by a child or the like. Thus, it is possible to prevent troubles caused by pulling out the power cord 20. For example, unplugging and plugging of the power cord 20 by a child or the like may cause a malfunction of an electric appliance connected to the power cord 20. In this case, such a malfunction can be prevented by issuing some kind of warning or by shutting off the power supply of the electric appliance so that power is not supplied.

In the second embodiment, a piezoelectric film having pyroelectricity such as PVDF can be used instead of PLLA. Using PVDF as the piezoelectric film makes it possible to add a function, such as advance detection of abnormal heat generation of the power cord. In terms of grip detection, PLLA can achieve higher sensitivity than PVDF.

Figure 8A:
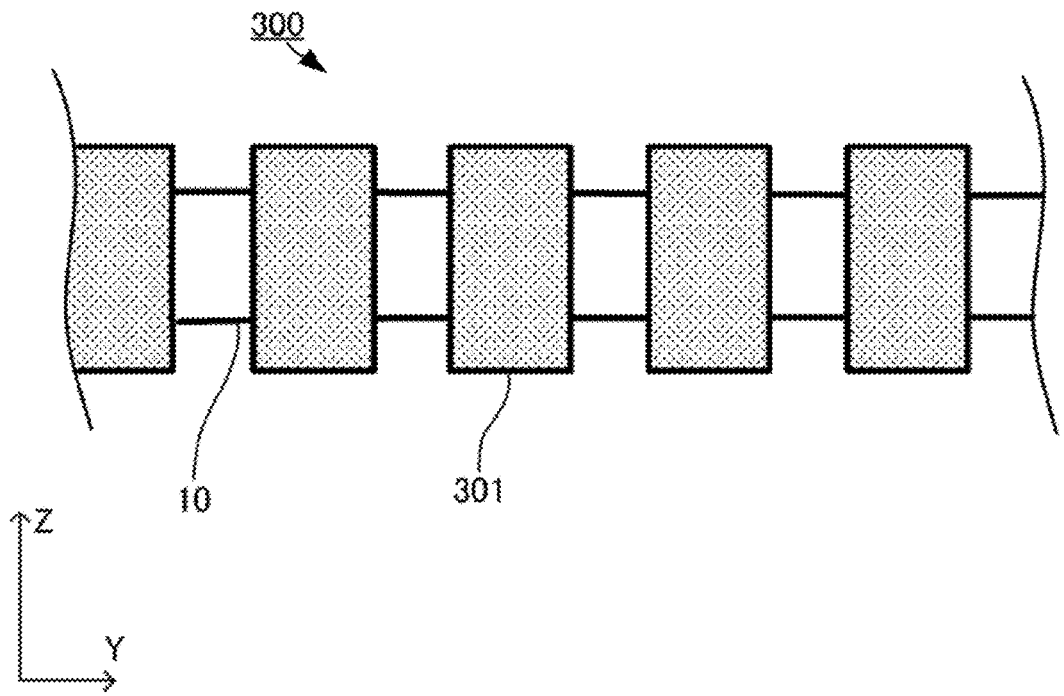
FIG. 8(A) is a partial side view of a grip detection sensor according to a first modification.
Figure 8B:
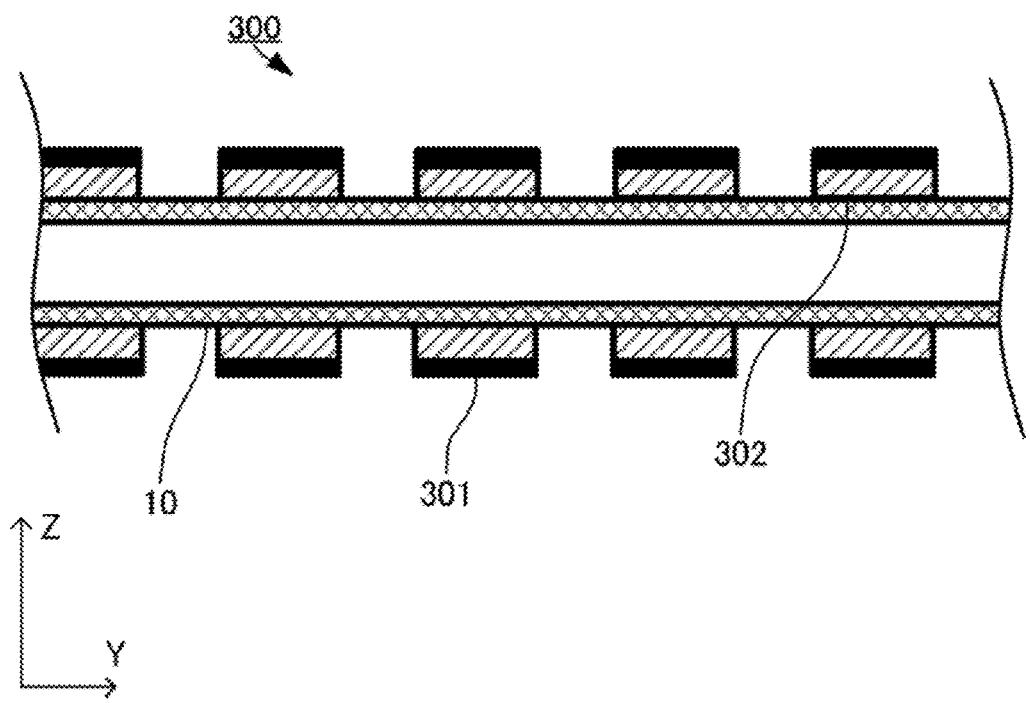
FIG. 8(B) is a schematic sectional view of the grip detection sensor according to the first modification taken along a line parallel to an axis of the grip detection sensor.
Figure 9A:
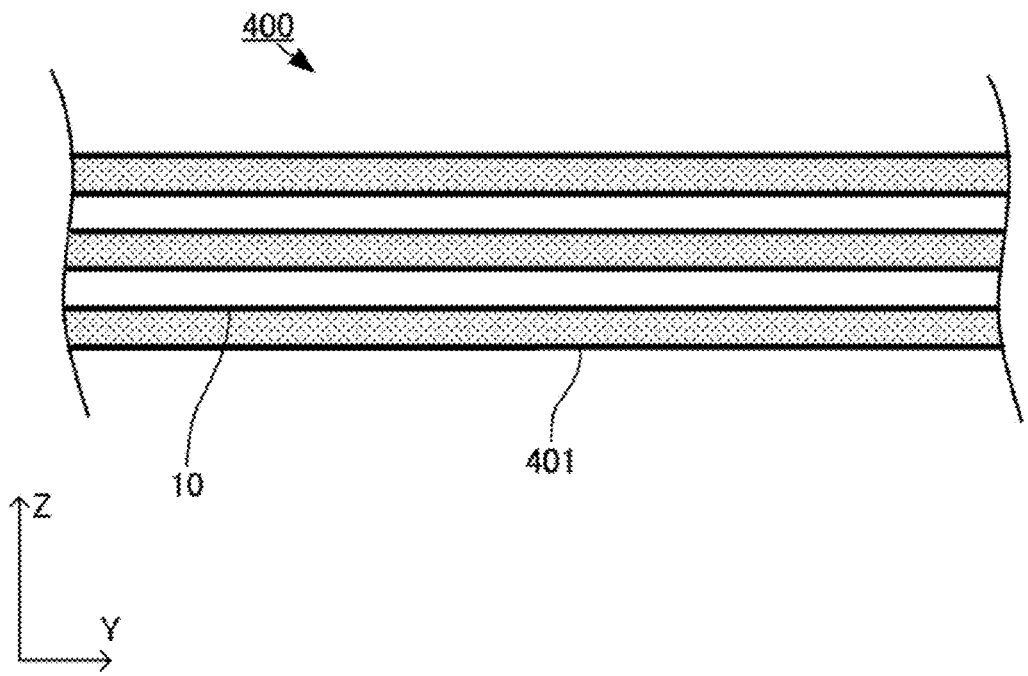
FIG. 9(A) is a partial side view of a grip detection sensor according to a second modification.
Figure 9B:
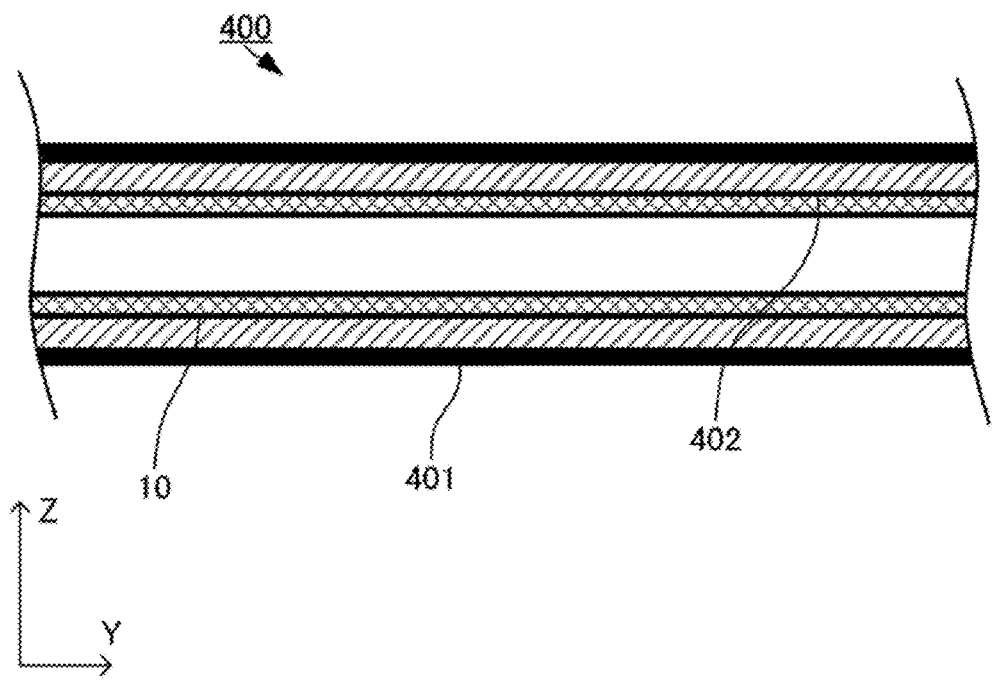
FIG. 9(B) is a schematic sectional view of the grip detection sensor according to the second modification taken along a line parallel to an axis of the grip detection sensor.
Figure 10A:
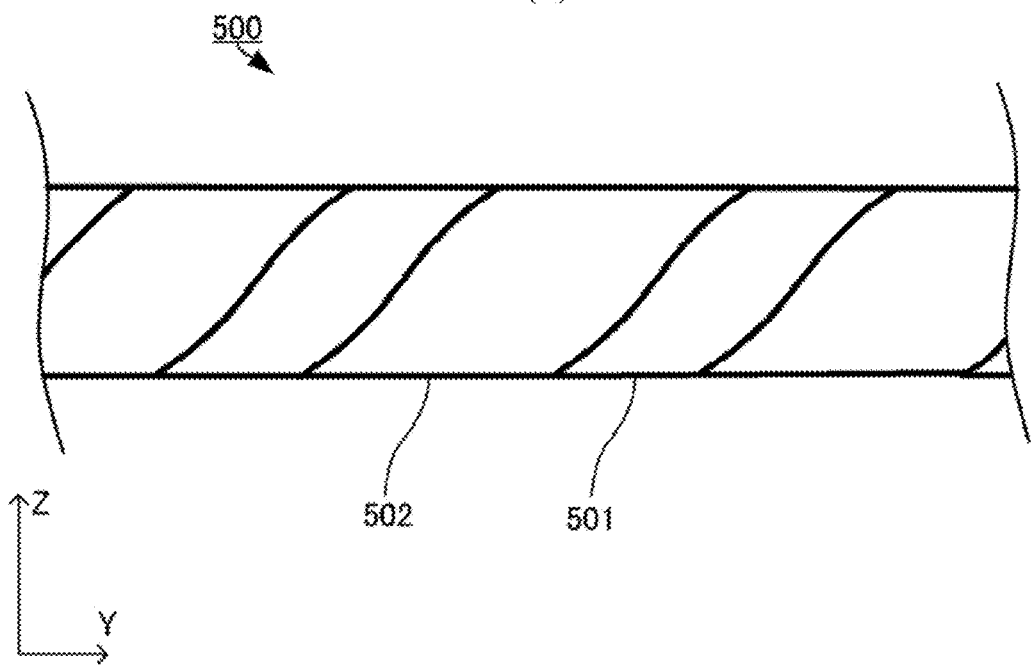
FIG. 10(A) is a partial side view of a grip detection sensor according to a third modification.
Figure 10B:
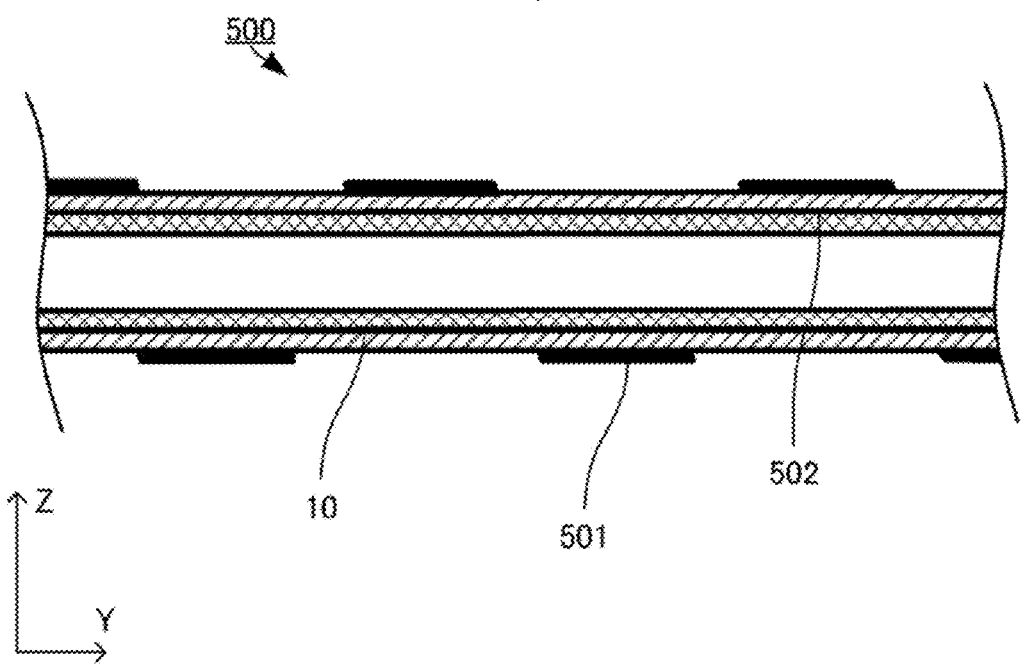
FIG. 10(B) is a schematic sectional view of the grip detection sensor according to the third modification taken along a line parallel to an axis of the grip detection sensor.

Hereinafter, a first modification, a second modification, and a third modification are described. FIG. 8(A) is a partial side view of a grip detection sensor 300 according to a first modification. FIG. 8(B) is a schematic sectional view of the grip detection sensor 300 according to the first modification taken along a line parallel to an axis of the grip detection sensor. FIG. 9(A) is a partial side view of a grip detection sensor 400 according to a second modification. FIG. 9(B) is a schematic sectional view of the grip detection sensor 400 according to the second modification taken along a line parallel to an axis of the grip detection sensor. FIG. 10(A) is a partial side view of a grip detection sensor 500 according to a third modification. FIG. 10(B) is a schematic sectional view of the grip detection sensor 500 according to the third modification taken along a line parallel to an axis of the grip detection sensor.

As shown in FIGS. 8(A) and 8(B), the grip detection sensor 300 according to the first modification has generally the same structure as that of the first embodiment except that piezoelectric elements 301 (piezoelectric films 31) and spacers 302 differ in shape from those of the first embodiment. Each of the piezoelectric elements 301 and the spacers 302 has an annular shape and is formed on the surface of the tube 10 so as to wind around the tube 10. The plurality of piezoelectric elements 301 and spacers 302 are provided at intervals in the axial direction of the tube 10. With this configuration, the grip detection sensor 300 can also appropriately detect whether or not the tube 10 is gripped by a patient, in the same manner as the grip detection sensor 100.

As shown in FIGS. 9(A) and 9(B), the grip detection sensor 400 according to the second modification has generally the same structure as that of the first embodiment except that piezoelectric elements 401 (piezoelectric film 41) and spacers 402 differ in shape from those of the first embodiment. Each of the piezoelectric elements 401 and the spacers 402 has a linear shape and is formed on the surface of the tube 10 in parallel to the axial direction of the tube 10. The plurality of piezoelectric elements 401 and spacers 402 are provided at intervals in the circumferential direction of the tube 10. With this configuration, the grip detection sensor 400 can also appropriately detect whether or not the tube 10 is gripped by a patient, in the same manner as the grip detection sensor 100.

As shown in FIGS. 10(A) and 10(B), the grip detection sensor 500 according to the third modification has generally the same structure as that of the first embodiment except that a spacer 502 differs in shape from that of the first embodiment. The spacer 502 has a cylindrical shape and is formed to entirely cover the periphery of the tube 10. With this configuration, the grip detection sensor 500 can also appropriately detect whether or not the tube 10 is gripped by a patient, in the same manner as the grip detection sensor 100. Further, the entire surface of the tube 10 is covered by the spacer 502, and thus the tube 10 is hardly bent, which can also prevent breakage of the tube 10.

In the present embodiments, a pressure sensor using a piezoelectric film is described as one example of a detection unit configured to detect deformation, but the detection unit of the present disclosure can also be achieved by a strain sensor, an optical sensor, or the like. The present disclosure does not limit the type of the sensors thereto, and any sensor that can detect deformation may be used.

Further, in the present embodiments, the tube and the power cord are cited as examples of the object to which the grip detection sensor is attached, but the object is not limited thereto, and the grip detection sensor described herein can be attached to any linearly shaped flexible objects, such as other lines and infusion pipes.

DESCRIPTION OF REFERENCE SYMBOLS

10: tube (object)
11: piezoelectric film
12: first electrode
13: second electrode
20: power cord (object)
100, 200, 300, 400, 500: grip detection sensor
102, 202, 302, 402, 502: spacer
111: first main surface
112: second main surface

The invention claimed is:
1. A grip detection sensor comprising:
a piezoelectric film having a first main surface and a second main surface, one of the first main surface and the second main surface being disposed at least partly on a periphery of a linearly shaped flexible object, wherein the piezoelectric film is wound around the periphery of the object;
a first electrode on the first main surface;
a second electrode on the second main surface; and
a spacer configured to maintain a space between the object and the piezoelectric film.
2. The grip detection sensor according to claim 1, wherein the spacer is a cushioning material having flexibility.
3. The grip detection sensor according to claim 2, wherein the spacer has lower rigidity than the object.
4. The grip detection sensor according to claim 1, wherein the object has a tubular shape.
5. The grip detection sensor according to claim 1, wherein the spacer entirely covers the periphery of the object.
6. The grip detection sensor according to claim 1, wherein the first electrode and the second electrode are transparent.
7. The grip detection sensor according to claim 6, wherein the first electrode and the second electrode are comprised of one of an inorganic material or an organic material.
8. The grip detection sensor according to claim 7, wherein the inorganic material is selected from one of ITO, ZnO, silver nanowire, carbon nanotube or graphene.

9. The grip detection sensor according to claim 1, wherein the piezoelectric film is composed of a transparent material.

10. The grip detection sensor according to claim 9, wherein the transparent material is selected from uniaxially stretched polylactic acid (PLA) or poly-L-lactic acid (PLLA), and the PLA or PLLA is uniaxially stretched in a direction that forms a predetermined angle with respect to a bending direction of the piezoelectric film, and wherein the piezoelectric film is disposed on the periphery of the object such that the grip detection sensor can detect deformation of the object.

11. The grip detection sensor according to claim 1, wherein the spacer is composed of transparent material.

12. A grip detection sensor comprising:
a piezoelectric film composed of a polymer having a piezoelectric constant greater than a predetermined threshold, the piezoelectric film comprising a first main surface and a second main surface, one of the first main surface and the second main surface being disposed at least partly on a periphery of a linearly shaped flexible object, wherein the piezoelectric film is wound around the periphery of the object;
a first electrode on the first main surface;
a second electrode on the second main surface; and
a spacer configured to maintain a space between the object and the piezoelectric film.

13. The grip detection sensor of claim 12, wherein the piezoelectric film is comprised of a material that is biaxially stretched, wherein two axes of the biaxial stretching are at different stretch ratios.

14. The grip detection sensor of claim 12, wherein a stretch ratio of the piezoelectric film is between 3 and 8.

15. The grip detection sensor according to claim 12, wherein the polymer is selected from polylactic acid (PLA), poly-L-lactic acid (PLLA) or PVDF.

16. The grip detection sensor according to claim 15, wherein the polymer is PLA or PLLA, and the PLA or PLLA is uniaxially stretched in a direction that forms a predetermined angle with respect to a bending direction of the piezoelectric film, and wherein the piezoelectric film is disposed on the periphery of the object such that the grip detection sensor can detect deformation of the object.

17. A grip detection sensor comprising:
a piezoelectric element disposed at least partly on a periphery of a linearly shaped flexible object, wherein a piezoelectric film of the piezoelectric element is wound around the periphery of the object;
a spacer configured to maintain a space between the object and the piezoelectric film; and
a processing unit configured to:
monitor voltage of an output of the piezoelectric element;
determine that the voltage has exceeded a predetermined threshold; and
issue a notification to a call system.

18. The grip detection sensor of claim 17, wherein the processing unit is further configured to:
detect a physical tremor when the voltage output vibrates at a frequency in a range of 5 Hz to 20 Hz; and
issue a notification to the call system.

19. The grip detection sensor according to claim 17, wherein the spacer is a cushioning material having flexibility and wherein the spacer has lower rigidity than the object.

* * * * *